United States Patent [19]

Tzeng

[11] 4,106,513
[45] Aug. 15, 1978

[54] DEVICE AND METHOD FOR THREE POINT ELECTRO THERAPY

[76] Inventor: J. C. Tzeng, 2801 S. King Dr., Apt. 1007, Chicago, Ill. 60616

[21] Appl. No.: 658,849

[22] Filed: Feb. 17, 1976

[51] Int. Cl.² .............................................. A61N 1/32
[52] U.S. Cl. ............................................... 128/420 R
[58] Field of Search .................. 128/404, 419 R, 420, 128/421, 422, 2.1 C, 2.1 R, 303.18, 1 C

[56] References Cited

U.S. PATENT DOCUMENTS

| | | | |
|---|---|---|---|
| 3,050,695 | 8/1962 | DuVall | 128/421 X |
| 3,721,246 | 3/1973 | Landis | 128/404 |
| 3,900,020 | 8/1975 | Lock | 128/2.1 C |
| 3,908,669 | 9/1975 | Manetal | 128/422 |
| 3,946,745 | 3/1976 | Hsiang-Lai et al. | 128/421 |
| 3,955,583 | 5/1976 | Horauf | 128/420 R |

FOREIGN PATENT DOCUMENTS

| | | | |
|---|---|---|---|
| 707,011 | 3/1965 | Canada | 128/419 R |
| 2,304,533 | 8/1974 | Fed. Rep. of Germany | 128/419 R |

OTHER PUBLICATIONS

Chisholm, "Acupuncture Analgesia", The Lancet, Sept. 9, 1972, p. 540.

Primary Examiner—Robert W. Michell
Assistant Examiner—Lee S. Cohen

[57] ABSTRACT

A device and method for use in the treatment of arthritic symptoms in joints, for example finger and wrist joints, whereby a pulsating, low voltage, direct current electricity is applied to the skin surface at three points, causing electricity to flow through the joint for the elimination of stiffness, soreness, discomfort and the like. The apparatus provides the electricity at pulsating rates through and about the joint. Convenient elastic rings may be used to secure surface electrodes to the skin at the joint.

4 Claims, 4 Drawing Figures

ATTACH TO SUBJECT

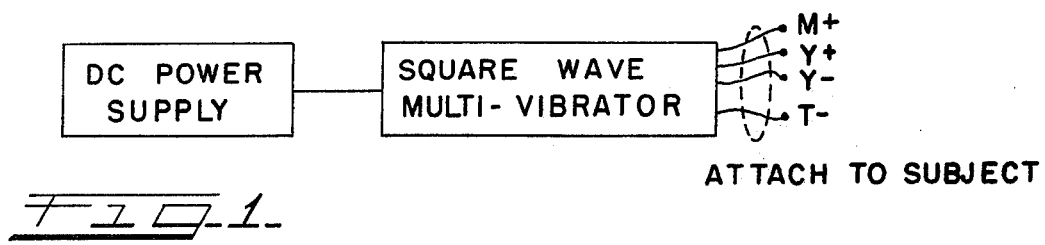
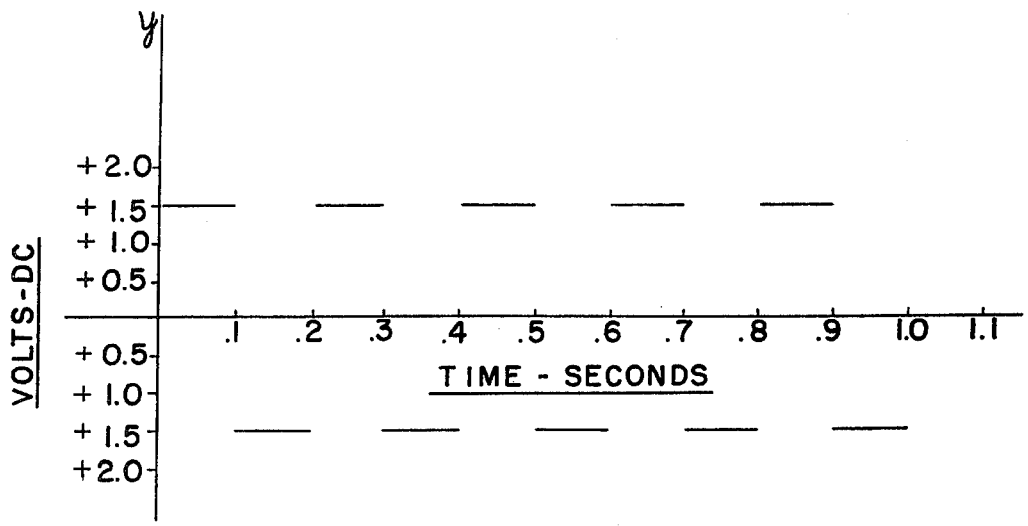
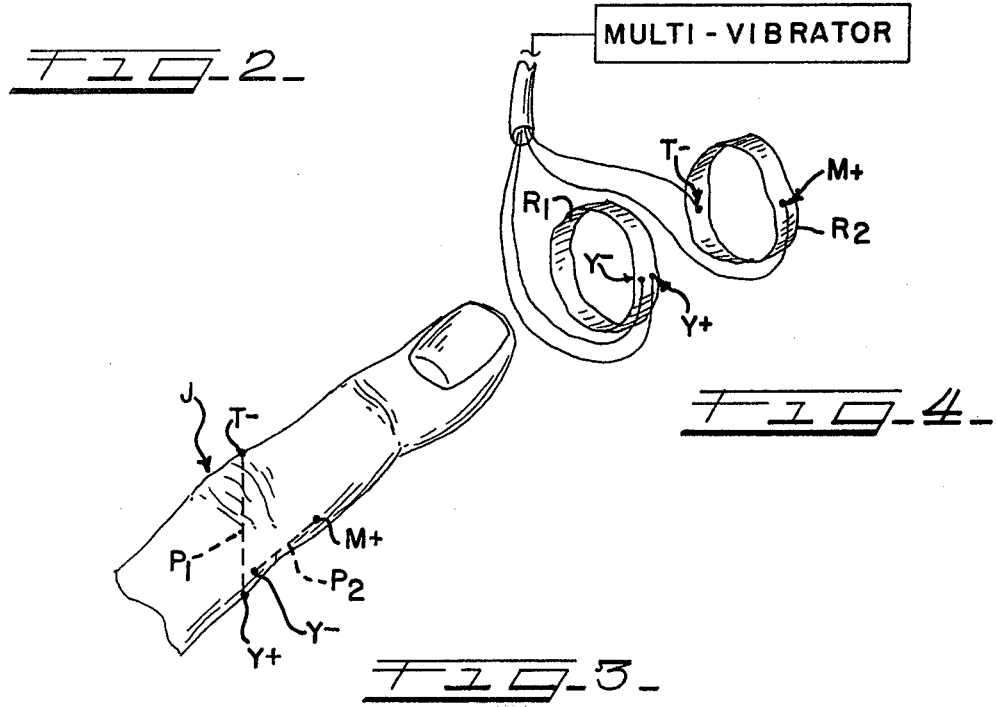

DEVICE AND METHOD FOR THREE POINT ELECTRO THERAPY

BACKGROUND OF THE INVENTION

1. Field of the Invention

This invention pertains to a healing and soothing device for use on a human or animal body to eliminate pain and discomfort at various points including arthritis, bursitis, neuralgia, rheumatism and the like in certain joints of the body.

2. Description of the Prior Art

Prior art to which this invention pertains is generally known by the term acupuncture which has been practiced by the Chinese for many thousand years. Only recently has this method of healing and curing become known and practiced on a limited basis in the United States. In the practice of acupunture, metal needles are inserted into certain sensitive areas in the body as are determined from experience or from monitoring points in the body having low resistance to electrical current. Such points are usually determined to be areas between the bone and adjacent muscle tissue. When the acupuncture point is located the insertion of the needle will relieve pain, discomfort and provide curing at associated points. While it is not known why acupuncture works, there are a number of theories postulated dealing with the chemical and electrical changes that occur upon the insertion of needles into certain body areas. It has been reasoned by the inventor herein that the use of needles per se in acupuncture is not mandatory and that the curing effect of acupuncture occurs from electrical changes that occur on an atomic level when electrons or other atomic or subatomic particles that have been distorted from their natural arrangment and accumulated are disbursed back into their prior, normal arrangement when metal needles are inserted to provide the necessary catalyst to urge the particles back to their normal structural arrangement. Because the changes are thought to be electrical in nature, insertion of needles is not mandatory. The electrical method disclosed herein can be used for re-arranging the distorted atomic structure to accomplish the same result as acupuncture, without piercing the skin. Thus, the present invention provides a method and apparatus for providing a treatment termed Surface Electro Therapy which provides certain of the benefits of acupuncture without the usual pain caused by inserting needles.

SUMMARY

This invention pertains to a three-point method called Surface Electro Therapy and to an apparatus, both of which are used for the treatment of bodily discomforts, stiffness, etc., caused by arthritis, rheumatism and the like. Low voltage electrical current is applied via three electrodes adjacent the treated area, usually a joint, in such a manner to provide two paths for passing current through the affected joint. A pulsating low voltage electrical current is used to prevent muscle fatigue and to permit the feeling of a steady flow of electricity yet prevent short circuiting between two closely positioned electrodes.

In practicing the invention disclosed herein in the treatment of joints such as finger joints, two electrical contacts or electrodes are placed adjacent the joint and radially or diametrically opposed about the finger and a third electrode is placed in position on the other side of the joint spaced from one of the first contacts on the same side of the finger but across the joint. With the electrical arrangement disclosed herein, direct current of a low voltage suggested between 1 and 3 volts is applied in a pulsating fashion to provide two continuous, pulsating current flow paths through the treated joint between the electrodes that are spaced across from one another. Such a three-point method of application of electrical flow has provided relief from stiff and aching joints.

These and other objects and advantages of the invention become apparent to a person having ordinary skill in the art with reference to the following drawings, description and claims.

DESCRIPTION OF THE DRAWINGS

FIG. 1 is a schematic block diagram illustration of the electrical circuitry involved with the method and apparatus disclosed herein;

FIG. 2 is an electrical diagram of the pulsing voltage generated by the electrical apparatus of FIG. 1;

FIG. 3 is representative of a portion of a human finger showing the positioning of the three point electrodes about the middle joint and the flow paths of electricity that are created; and, FIG. 4 is an illustration of finger attaching members used to apply the electrodes about a joint for treatment.

DETAILED DESCRIPTION

Referring now to the drawings, and in particular to FIG. 1, there is shown an electrical schematic diagram designating a DC current power supply such as would be provided by a number of small batteries each generating 1.5 volts of direct current. It is suggested that a voltage in the range of 1 to 3 volts is sufficient for the treatment described herein to eliminate arthritic or other discomforting symptoms in a joint. Voltage of a higher magnitude can cause a pain sensation which is undesirable and not necessary to produce relief. Also shown in FIG. 1 is a block diagram designation of a square wave multivibrator such as would be provided by any well-known solid state or tube device or an electromechanical relay that could be used to provide the necessary voltage on a pulsating or intermittent basis.

The voltage applied herein is of the 1.5 volt magnitude and has an on duration of approximately 100 milli seconds and an off duration of 100 milli seconds and then repeats 5 of such cycles in each second (see FIG. 2). Such a pulsing sequence provides a physical or biological sensation of continuous current flow while retaining the healing benefits of pulsating current without muscle fatigue. The multivibrator also produces a negative voltage that is pulsed or spaced between each burst of positive voltage as shown in FIG. 2. Thus, as shown in FIG. 2, when the positive voltage at the top half of the X axis is providing positive voltage, there is no corresponding negative voltage; however, between each burst of positive voltage there is a burst of negative voltage. As will be seen, this phasing of the pulses of voltage prevents short circuiting of two adjacent electrodes and insures constant current flow at the joint.

In the application of voltage to the human body an example will be explained with reference to a finger joint. The invention is not limited to an application with a finger joint but also can be used with other arthritic or irritated joints of the body, including the hand, fingers and the wrist, shoulder, back, knee and the like. The finger and wrist joints are more adapted to healing with the application of low voltage pulses because there is relatively more spacing, i.e., low resistance to the passage of electricity between the adjacent bone members than is present with other large, tight joints such as the hip joint and elbow joint.

Application of the low voltage electricity for soothing and curing purposes is based on application of low voltage electrical current at three points about a joint. Thus with reference to the finger joint J illustrated in FIG. 3 for purposes of illustration, it is noticed that a first electrode designated M+ is placed above the joint J and a corresponding second electrode Y− is located on the same side of the finger on the opposite side of the joint from electrode M+. A third electrode Y+ is closely spaced with electrode Y− across the finger joint from the electrode M+. A fourth electrode T− is on the same side as first electrode M+ but located above joint J. A single electrode could be used for Y+ and Y− since only positive or negative voltage passes at one time. As shown in FIG. 4, these electrodes may be attached about the finger joint by mounting the associated wires and electrodes in elastic, rubber or other convenient ring or clip type of members designated R1, R2. Further, to improve the conductivity between each electrode M+, T−, Y+, Y−, on the skin an EKG or electrolyte conducting jelly may be applied to the finger prior to application of the electrodes.

After application of the electrodes about the finger joint J in the triangular three-point fashion illustrated in FIG. 3 the multivibrator is switched on to apply the pulsating direct voltage across the joint through two paths P1, P2. It is anticipated that the multivibrator will be adjustable to vary the amount of applied voltage from one volt to approximately 4.5 volts, depending on the individual tolerance of each user.

With the application of voltage across the irritated or stiffened joint J, it is noticed that two electrical paths are provided and designated by the dotted lines P1 and P2. Thus when point Y+ has a positive charge of electricity and point T− has a negative charge of electricity, an electrical flow path P1 will be established between Y+ and T−. Similarly, when Y− has a negative electrical charge and M+ has a positive electrical charge, a second flow path P2 will be established between M+ and Y−. To prevent a flow path from existing between Y− and Y+, a pulsating form of direct voltage is applied. Thus, when Y+ has a positive charge, electricity is flowing from Y+ to T−; however, there is no electrical flow existing between Y− and the positive M+ to cause a short circuit between Y+ and Y−. For example, if the path P1 is being provided with electrical flow of positive voltage illustrated by the top half pulsating voltage shown in FIG. 2, the second flow path P2 is alternately being provided with no pulsating voltage as illustrated by the lower half of FIG. 2. Hence, it is noticed that when path P1 receives a burst of voltage there is no corresponding voltage existing in flow path P2, thus there is no chance of a short circuit or flow of current between Y− and Y+. This unique alternate pulsing of the three-point application provides a unique, continuous flow of electrical current through the joint area for healing purposes.

This use of the method and apparatus of this invention is not limited to treatment of joint disorders but the three-point method of treatment may be used for the treatment of muscular and skeletal diseases and pain syndrome. For example, in the treatment of migraine headaches, Y+ and Y− are applied at the shoulder joint with M+ and T− applied at the temporal region. Thus the electrodes are applied in the same location where acupuncture needles have previously been inserted.

Similarly, where acupuncture needles have been previously used for insertion into the skin to produce healing effects, the three-point electrode system disclosed herein may now be used.

The foregoing description and drawings merely explain and illustrate the invention and the invention is not limited thereto, except insofar as the appended claims are so limited, as those who are skilled in the art who have the disclosure before them will be able to make modifications and variations therein without departing from the scope of the invention.

What is claimed is:

1. An apparatus for providing electric current at a low voltage to a body for healing purposes, the improvement comprising:

a power supply of positive and negative direct current voltage;

means for converting said voltage into pulsating form and including means for alternating pulses of positive and negative voltage to prevent simultaneous supply of both positive and negative voltage;

electrode means for contact with said body; and, conductor means electrically connecting said electrode means with the means for alternating pulses;

said electrode means including first electrode means for contact with the surface of said body to create a first electrical flow path with said pulses of positive voltage, and, said electrode means including second electrode means for contact with said body in proximity with the first electrode means to create a second electrical flow path with said pulses of negative voltage whereby said first and second flow paths allow for electric current to pass through said body in an alternating, pulsating rate.

2. The apparatus of claim 1, wherein said electrode means includes:

a first holder and a second holder, each holder including means for attachment to said body, said holders having means for mounting said first electrode means and said second electrode means thereon.

3. A method of treatment of a body comprising the steps of:

providing a direct current positive and negative voltage;

pulsing said voltage into intermittent pulses;

phasing said pulses to alternately provide positive and negative voltage;

providing electrode means to conduct said positive and negative voltages in two paths in proximity to one another;

connecting the electrode means electrically with said alternating voltages;

attaching said electrode means to said body for said treatment; and producing said alternating voltages at the electrode means to pass a pulsating, alternating positive and negative current through said body.

4. The method of treatment of claim 3, and:

providing said positive and negative voltage in the range of ± 1.0 to ± 4.5 volts; and pulsing said positive and negative voltage at between 4 and 10 pulses per second.

* * * * *